United States Patent [19]
Wendel et al.

[11] Patent Number: 5,891,728
[45] Date of Patent: Apr. 6, 1999

[54] TEST FOR DETERMINING PYROGENIC EFFECT OF A MATERIAL

[75] Inventors: Albrecht Wendel, Im Buckenloh 19, Tubingen, Germany, D-72070; Thomas Hartung, Glarnischstrahe, 17, Constance, Germany, D-78464

[73] Assignees: DPC Biermann GmbH, Bad Nauheim; Albrecht Wendel, Tulingen; Thomas Hartung, Constance, all of Germany

[21] Appl. No.: 643,126

[22] Filed: May 2, 1996

[30] Foreign Application Priority Data

May 3, 1995 [DE] Germany ............... 195 16 247.1

[51] Int. Cl.$^6$ ................................... G01N 31/00
[52] U.S. Cl. ................... 436/2; 436/63; 436/86; 530/351
[58] Field of Search .................. 436/2, 18, 63, 436/86; 435/2; 530/351

[56] References Cited

U.S. PATENT DOCUMENTS

| | | | |
|---|---|---|---|
| 3,944,391 | 3/1976 | Harris et al. | 435/18 |
| 4,434,237 | 2/1984 | Dinarello | 436/63 X |
| 5,474,769 | 12/1995 | Grabstein et al. | 424/85.2 |
| 5,506,218 | 4/1996 | Parker et al. | 514/78 |
| 5,545,623 | 8/1996 | Matsumori | 514/26 |
| 5,550,132 | 8/1996 | Benson et al. | 514/269 |

OTHER PUBLICATIONS

Allen et al. *Journal of Laboratory & Clinical Meidicine*, vol. 119, No. 5, May 1992, pp. 538–546.
Yentis et al. *Cytokine*, vol. 6, No. 3, May 1994, pp. 247–254.
Dinarello et al. *Brain Research*, vol. 562, 1991, pp. 199–206.
Strieter et al. *Journal of Leukocyte Biology*, vol. 47, 1990, pp. 366–370.
Desch et al. *Lymphokine Research*, vol. 8, No. 2, 1989, pp. 141–146.

*Primary Examiner*—Maureen M. Wallenhorst
*Attorney, Agent, or Firm*—Jacobson, Price, Holman & Stern PLLC

[57] ABSTRACT

A method of ascertaining the pyrogenicity of a material involves exposing to the material a sample of whole blood from a human or an amimal, followed by determining whether the exposure induces formation of endogenous pyrogen in the sample.

20 Claims, 4 Drawing Sheets

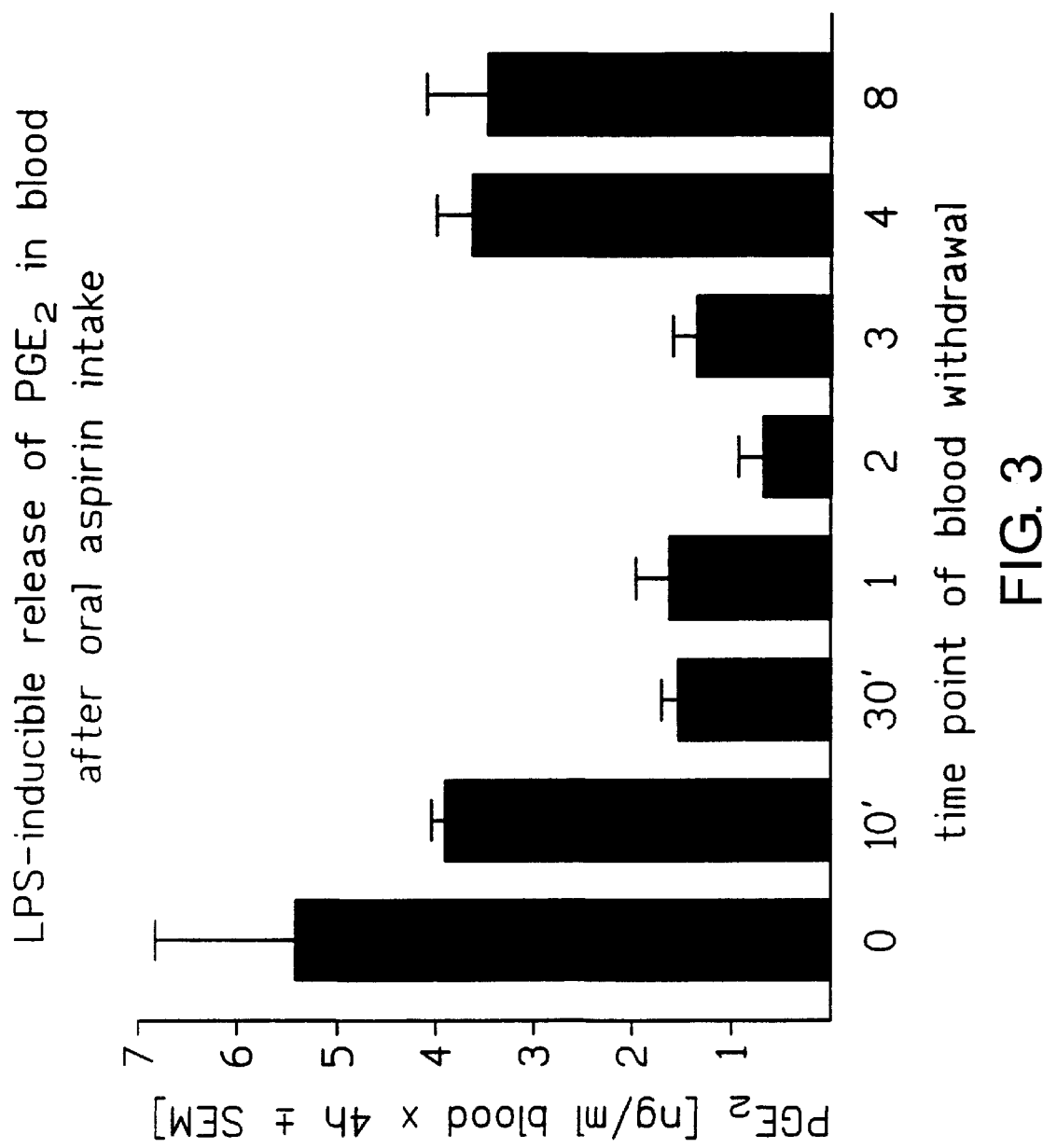

TEST FOR DETERMINING PYROGENIC EFFECT OF A MATERIAL

The present invention represents a procedure for testing the pyrogenicity of materials, such as chemical and biological compounds.

It is known that, when brought into contact with human organisms, chemical or biological compounds initiate pyrogenicity, partly because they are pyrogenic as such or because they contain pyrogenic components. Compounds with such a risk potential include medicinal drugs, especially products that can be inhaled, injected or infused, including blood replacement or blood exchange materials, plastics of different physical states, including dispersions, cosmetic products or medical devices such as membranes or artificial denture. Even nutrients can represent a risk of pyrogenicity. Usually, compounds that act as a pyrogenic via contact with human tissue, cells or body fluid are designated as compounds having exogenous pyrogenic action, independently of the potential endogenous origin of the pyrogenic part of the compound under consideration. In this sense, the following description uses the terms exogenous pyrogen and compounds with exogenous pyrogenic action, synonymously, to represent the subject of the pyrogen test invention.

The public is aware of the need for pyrogen testing. In order to assure safety and in order to identify individual lots that are probably contaminated, a continuous single testing of a certain products in animal experiments is required by law.

Among the compounds causing fever, one of the best described is endotoxin (lipopolysaccharide, LPS), which comes from the bacterial wall of Gram-negative germs (Moltz et al., *Neurosci. Biobehav. Rev.*, 1993, 17, 237–269; Tilders et al., *Psychoneuroendocrinology*, 1994, 19, 209–232; Rothwell, *Crit. Rev. Neurobiol.*, 1994, 8, 1–10; Zeisberger and Roth, *Neuropsychobiology*, 1993, 28, 106–109). It was, therefore, obvious to replace animal experiments, which were usually performed with rabbits, with a direct endotoxin assay (Limulus assay, LAL). This approach has obvious limitations; only endotoxins as possible initiators of fever are detected; stimulators of leukocytes that can also induce fever escape detection. The assay is disturbed by endotoxin-binding components that are present in blood or blood components (Harris et al, *J. Lab. Clin. Med.*, 1991, 118, 186–193; Emancipator et al., 1992, *Infect. Immun.*, 60, 596–601; Read et al., *Eur. Heart J.*, 1993, 14, 125–129). Some of these endotoxin-binding components withdraw LPS from being detected in the Limulus assay, while, on the contrary, they potentiate the reaction with leukocytes, i.e., the primary pyrogenic reaction. Essentially, testing for exogenous pyrogens in blood products is a very frequent routine case. On the other hand, the Limulus assay is so sensitive that it is easily prone to false positive results, due to impurities that are not relevant to product quality (Fujiwara et al., *Yakugaku Zasshi*, 1990, 110, 332–340).

Also, on the other hand, the in vivo rabbit test is problematic. The immune reaction (fever) to a given stimulus varies considerably from species to species. It is open whether or not the rabbit is representative of other mammals, including humans, because the sensitivity to endotoxin is known to vary by a factor of 10,000 between various species. For pyrogenic components other than endotoxin, no such investigations are available.

It is the purpose of the present investigation to provide a procedure that allows the detection of a broad variety of pyrogenic compounds. The procedure needs to be simple and to be carried out at low costs. Further advantages will follow, especially from the advantages that are planned.

The solution of the task for investigating pyrogenic effects of a material is characterized by bringing the material into contact with whole blood and checking for the formation and release of endogenous pyrogens.

BRIEF DESCRIPTION OF THE DRAWINGS

FIG. 3 shows the formation of endogenous pyrogens in human blood culture induced by various stimuli of the immune reaction.

DESCRIPTION OF THE PREFERRED EMBODIMENTS

Figure 1:
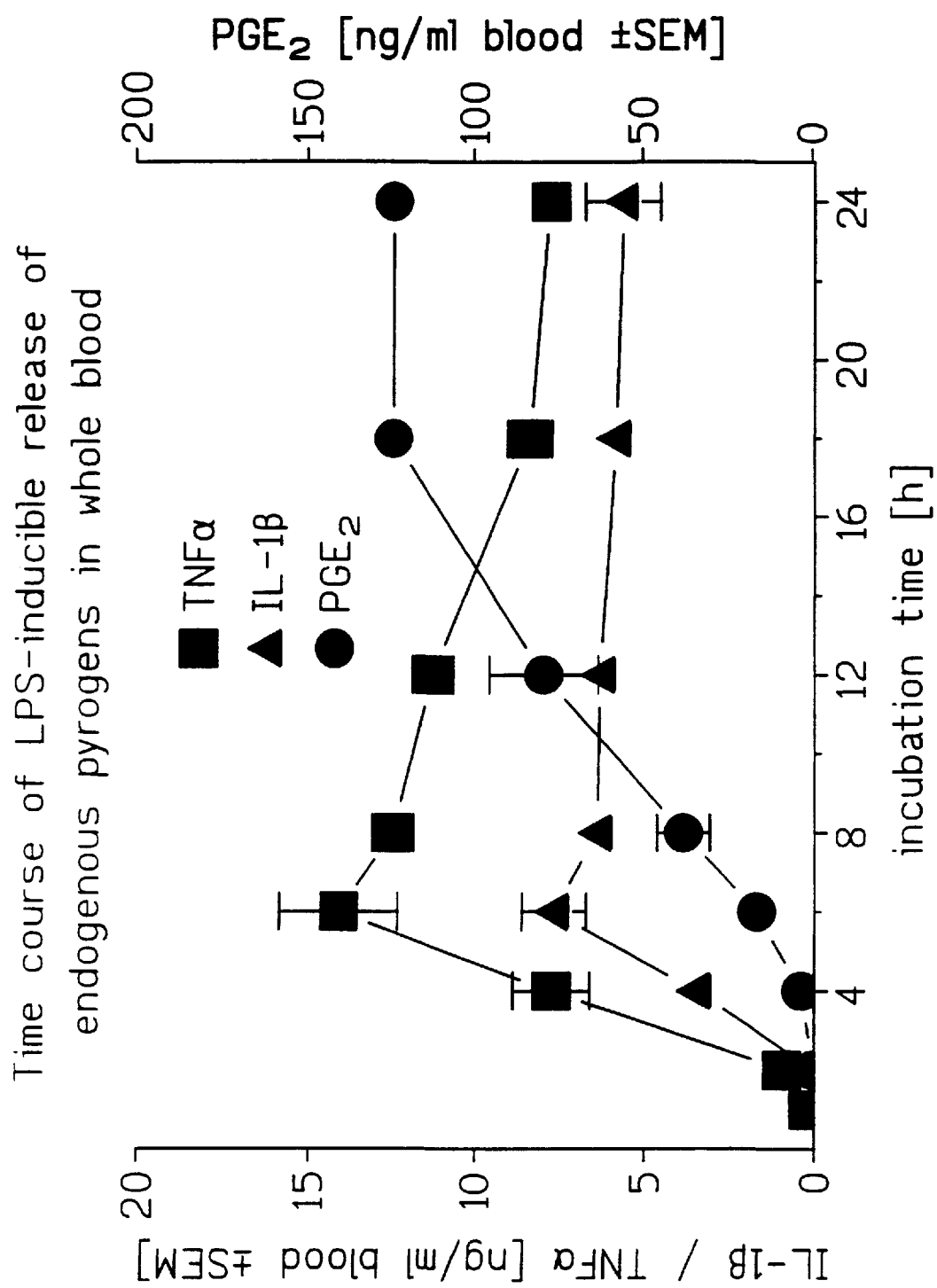
FIG. 1 shows a time course of the endotoxin-induced formation of endogenous pyrogens in human blood culture.

The special advantage of the present procedure is the use of a biological system that allows making relevant assessments of the exposure of humans and animals (including non-human mammals) to exogenous fever-reducing agents from any source. Parameters to be measured are the endogenous pyrogens. These are messenger compounds of the immune system that mediate the fever reaction and represent the message of the organism that a exogenous pyrogen has been recognized. This class of compounds contains, e.g., cytokines or colony stimulating factors or growth factors. The most important known endogenous pyrogens are the proteins interleukin-1 (IL-1), interleukin-6 (IL-6), and tumor necrosis factor (INF), as well as low molecular weight lipid mediators such as prostaglandin $E_2$ ($PGE_2$). One routine assay for IL-1, IL6, or TNF is ELISA (Enzyme-Linked Immunosorbent Assay), and one for $PGE_2$ is EIA (Enzyme Immuno Assay).

Leukocyte population isolated from blood could pose a biological system for detecting exogenous pyrogens. Most isolation procedures, however, are too complicated for routine testing of compounds. It is, therefore, easier to use for pyrogen-detecting purposes human or animal whole blood such as, e.g., freshly contained blood from human healthy donors, without separation of single components or cells. In this system leukocytes are in their natural composition and environment and all serum components are present that can influence the actions of exogenous pyrogens. A special advantage is that components can be added to whole blood that retard or prevent blood clotting, such as, e.g., citrate, in a final concentration of 0.38% or heparin (sodium heparinate) that can be used during the incubation without affecting or falsifying the reaction described for the invention.

It has been found to be useful to dilute the whole blood for instance to 20% of the original concentration with cell culture medium or with physiological sodium chloride solution. It is needless to say that any technical device used, such as laboratory equipment or compounds to be added including anti-thrombotics or dilutives, has to be free of exogenous pyrogens. During the incubation, where, preventatively, antibiotics such as penicillin, streptomycin, chloramphanicol, amphotericin or combinations of them can be present, a relevant contamination has to be excluded.

An example for the release of endogenous pyrogens are the four endogenous pyrogens mentioned above which are released in response to compounds from the walls of Gram-negative or Gram-positive bacteria. The present procedure is highly sensitive to endotoxin, i.e., pg/ml amounts are able to effect release of endogenous pyrogens, and it is largely independent of the blood donor. As a positive control, preparations of endotoxin or lipoteichoic acid from the Gram-negative or Gram-positive bacterial cells walls, respectively, can be used. Pyrogen-free physiological sodium chloride solution for clinical use serves as a negative control.

For the detection of the time course of the release of endogenous pyrogens from whole blood as initiated by endotoxin, blood from seven healthy donors was diluted with cell culture media in a ratio of 1:5 and stimulated by 10 μg/ml LPS (FIG. 1). All factors were detected with commercially available ELISAs after incubation of 37° C. (date given in mean values±standard error of the mean S.E.M.), while unstimulated blood failed to release any of these factors. The amount of IL-1β detected reached a plateau after 6 h. The concentration of $PGE_2$ detected increased continuously until 24 h after incubation as did the LPS-induced amount of IL-6 (measured after 4, 10 and 24 h, data not shown). Unlike these factors, the TNF release showed a maximum at 12 h after stimulation with LPS. Since after 24 h the major part of TNF was still detectable, this time was chosen as a standard incubation time.

Figure 2A:
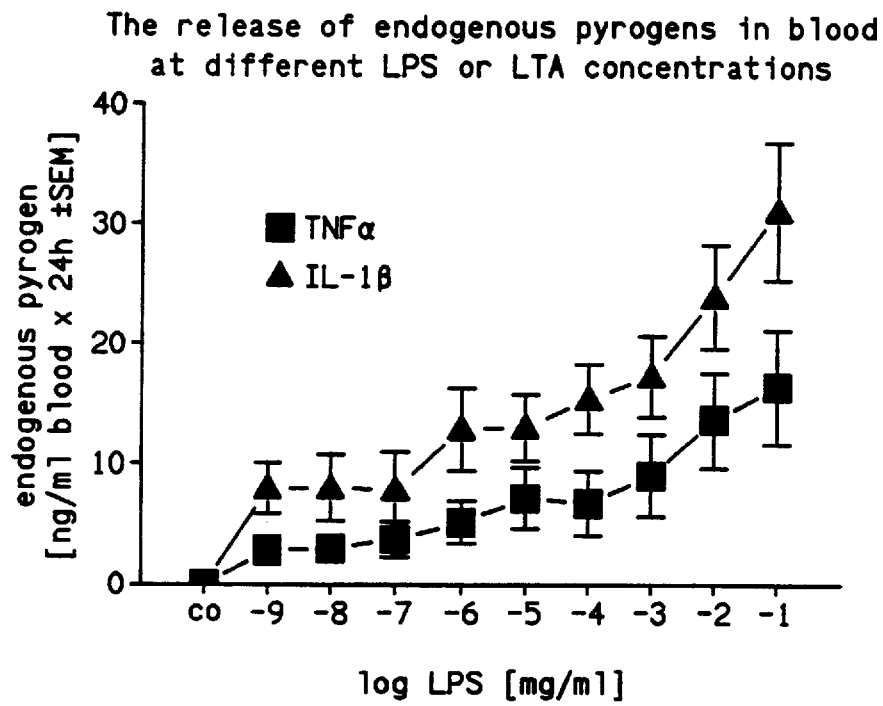
FIGS. 2a and 2b show the concentration dependency of the endotoxin-induced and lipoteichoic acid-induced formation of endogenous pyrogens in human blood culture.
Figure 2B:
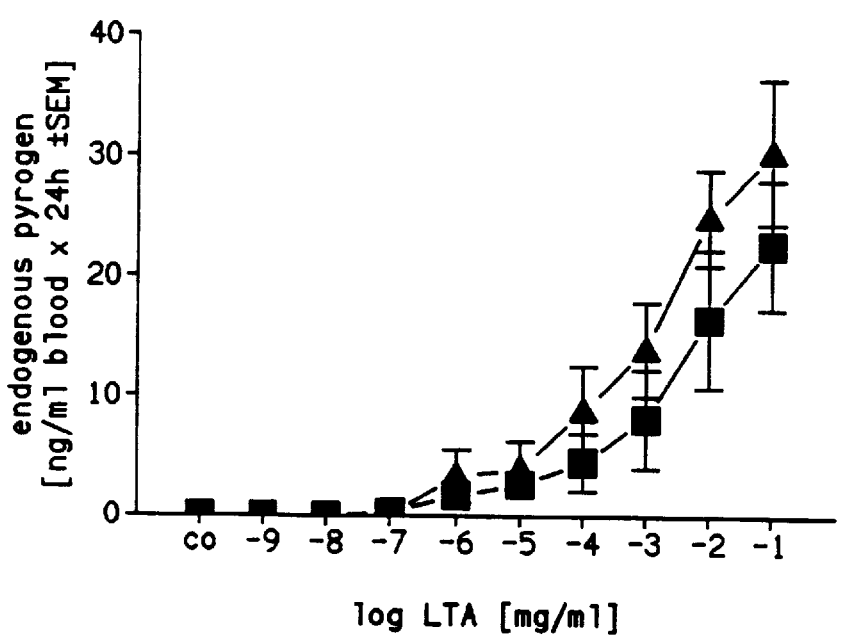

For determining the concentration dependence of the formation of endogenous pyrogens in human whole blood as initiated by Gram-negative component endotoxin and Gram-positive component lipoteichoic acid, blood from five healthy donors was diluted 1:5 and incubated for 24 h in the presence of endotoxin (LPS) or lipoteichoic acid (LTA) in the concentrations given, respectively. Cytokines were determined by ELISA and the data given as means±SEM (FIG. 2). In fact, the lowest concentration of endotoxin used, i.e., 1 pg/ml, induced significant formation of endogenous pyrogens, while the solvents for LPS and LTA, respectively, were without effect. These data demonstrate that human blood reacts very sensitively and in a concentration dependent manner to LPS and LTA.

Also, immune stimulators other than the ones described above can be detected as initiators of endogenous pyrogen formation by the procedure described. As an example, heat killed Gram-positive bacteria (*Staphylococcus aureus*) or their components (muropeptide, lipoteichoic acid, enterotoxins, streptolysin O) initiate a similar reaction (FIG. 3). Also, further immune stimulators, such as the plant component phytohemagglutimin or phorbolester, initiate the release of endogenous pyrogens.

The present procedure includes a large variety of advantages. It is based on the body's own primary reaction of forming endogenous pyrogens after exposure to exogenous pyrogens. All blood components are present that are needed for an interaction of the exogenous pyrogen with leukocytes (e.g., LPS binding protein—LBP, bactericidal permeability increase protein—BPI, soluble CD 14, defensines, etc.). The human or animal blood cells remain in their natural composition and surrounding. Preparation artifacts, as known to occur with isolated leukocytes, or dedifferentiations known to occur with cell lines, are unlikely to take place in this procedure. The procedure is very sensitive, i.e., it detects pg amounts of LPS. Moreover, a large variety of potential exogenous pyrogens other than endotoxin are detected. The procedure allows, also, investigating pharmacological effects of fever reduction in vitro or ex vivo.

Figure 4:
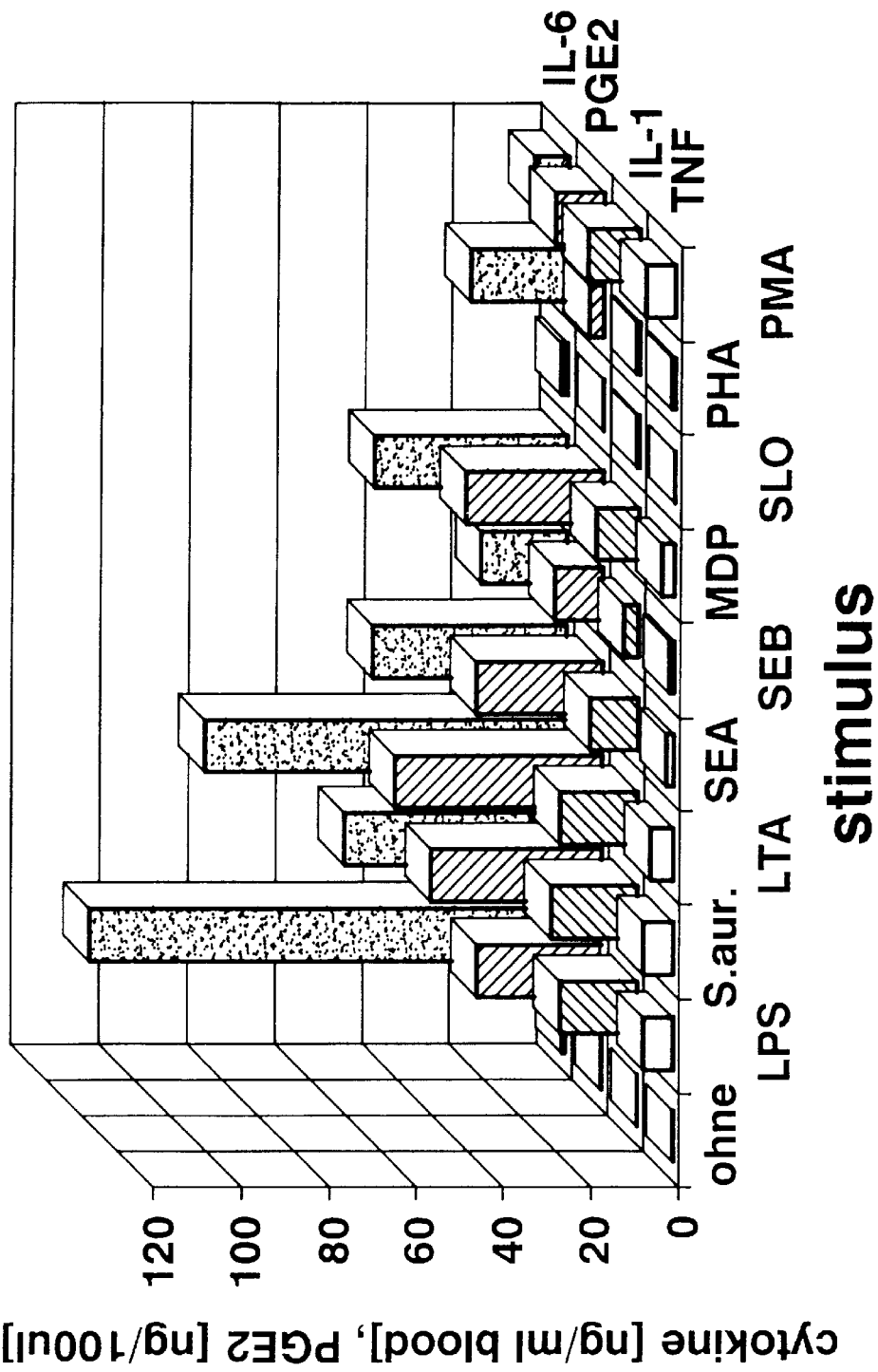
FIG. 4 shows the ex vivo endotoxin-induced formation of $PGE_2$ in human blood culture from aspirin-treated donors.

For instance, the procedure is suitable to check the consequence of a fever reducing therapy in humans or in animals. Blood was taken from three healthy volunteers that had ingested an anti-pyrogenic drug at time 0, in this case one tablet of aspirin (500 mg). When this blood was stimulated ex vivo with an exogenous pyrogen, such as 10 μg/ml LPS, the amount of $PGE_2$ inducible decreased very quickly and reached control values after some hours (FIG. 4). The amount of PGE was assayed by an EIA (middle value±SEM).

EXAMPLE

Citrate blood from healthy donors was diluted 1:5, immediately after withdrawal, with cell culture medium RPMI 1640 (Biochrom, Berlin). Heparin was added [2 IE/ml end concentration] (Liquemin®, Hoffmann La Roche, Grenzach-Whylen) in order to prevent clotting via recalcification. Stimuli were added simultaneously or were already present in the cell culture medium. The following compounds were used in the following maximum concentrations: LPS from *Salmonella abortus equi* [10 mg/ml], enterotoxin A (SEA) and B (SEB) from *Staphylococcus aureus* [1 μg/ml], lipoteichonic acid (LTA) from *S. aureus* [10 μg/ml], heat-killed *S. aureus* [0.001% cells v/v], streptolysin O (SLO) from *Streptococcus pyogenes* [2.5 units/ml], muramyldipeptide (MDP) [10 μg/ml], phytohemagglutinin M (PHA) [15 μg/ml], and phorbolester (PMA) [100 nM]. All stimuli except MDP (Bachem, Heidelberg) were purchased from Sigma (Deisenohofen). The incubations were carried out in open polypropylene reaction vials (Eppendorf, Hamburg) at 370° C. and 5% $CO_2$ for a standard incubation time of 24 h (Wilson et al., *J. Immunol. Meth.*, 1991, 139, 233–240). Cell-free supernatants were removed after centriguation (30000 G, 1 min) and stored at −80° C. until cytokine or prostaglandin determination.

Mediators released were measured with commercially available ELISAs: IL-1, IL6, and TNF were determined by assays from R & D Systems (H. Biermann, Bad Nauheim, Germany), while for determination of $PGE_2$ an assay from Cayman (SPI-Bio Europe, France) was used.

What is claimed is:

1. A method for evaluating safety or possible contamination of a product for use with humans or animals, by a pyrogen test comprising the steps of:

exposing a product intended for use with humans or animals to whole blood of a human in vitro or an animal in vitro; followed by subjecting a sample of the whole blood to an assay to determine whether the exposure induces formation of endogenous pyrogen in the sample;

whereby, the formation of endogenous pyrogen indicates the presence of an exogenous fever inducing agent in said product.

2. The method of claim 1 wherein the product has an unknown exogenous pyrogenic effect, the exposing step is performed in vitro on the sample of the whole blood, and the assay determines whether the product induces formation of endogenous pyrogen in the sample.

3. The method of claim 1 wherein the sample of whole blood includes components that prevent or retard blood clotting.

4. The method of claim 3 wherein the sample of whole blood includes a diluent.

5. The method of claim 4 wherein the diluent is cell-culture medium, physiological sodium chloride solution, or a mixture thereof.

6. The method of claim 3 wherein the endogenous pyrogen is interleukin-1.

7. The method of claim 3 wherein the endogenous pyrogen is interleukin-6.

8. The method of claim 3 wherein the endogenous pyrogen is tumor necrosis factor.

9. The method of claim 3 wherein the endogenous pyrogen is prostaglandin $E_2$.

10. The method of claim 1 wherein the sample of whole blood includes a diluent.

11. The method of claim 10 wherein the diluent is cell-culture medium, physiological sodium chloride solution, or a mixture thereof.

12. The method of claim 10 wherein the endogenous pyrogen is interleukin-1. interleukin-6, tumor necrosis factor, or prostaglandin $E_2$.

13. The method of claim 1 wherein the endogenous pyrogen is interleukin-1.

14. The method of claim 1 wherein the endogenous pyrogen is interleukin-6.

15. The method of claim 1 wherein the endogenous pyrogen is tumor necrosis factor.

16. The method of claim 1 wherein the endogenous pyrogen is prostaglandin $E_2$.

17. The method of claim 1 wherein the product is a medicinal drug.

18. The method of claim 17 wherein the medicinal drug is injectable or infusible.

19. The method of claim 1 wherein the product is a medical device.

20. The method of claim 1 wherein the product is a cosmetic.

* * * * *